United States Patent
Landes

(10) Patent No.: US 9,186,159 B2
(45) Date of Patent: *Nov. 17, 2015

(54) DISCECTOMY INSTRUMENT

(71) Applicant: GLOBUS MEDICAL, INC., Audubon, PA (US)

(72) Inventor: Glen Brian Landes, Quakertown, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/542,691

(22) Filed: Nov. 17, 2014

(65) Prior Publication Data

US 2015/0073418 A1    Mar. 12, 2015

Related U.S. Application Data

(63) Continuation of application No. 13/763,082, filed on Feb. 8, 2013, now Pat. No. 8,915,936, which is a continuation of application No. 12/710,796, filed on Feb. 23, 2010, now Pat. No. 8,394,101.

(60) Provisional application No. 61/154,610, filed on Feb. 23, 2009.

(51) Int. Cl.
*A61B 17/32* (2006.01)
*A61B 17/16* (2006.01)
*A61B 17/00* (2006.01)

(52) U.S. Cl.
CPC .......... *A61B 17/1671* (2013.01); *A61B 17/1617* (2013.01); *A61B 17/1633* (2013.01); *A61B 17/1659* (2013.01); *A61B 17/32* (2013.01); *A61B 2017/00261* (2013.01); *A61B 2017/320008* (2013.01)

(58) Field of Classification Search
CPC ................. A61B 2017/00261; A61B 17/1617; A61B 17/1633; A61B 17/1659; A61B 17/1671; A61B 17/32; A61B 17/320008
USPC .............. 30/164.9, 164.95; 81/177.7, 177.75, 81/177.8; 83/771–775; 403/122, 127, 131; 606/79–85, 86 R, 99, 167–180
See application file for complete search history.

(56) References Cited

U.S. PATENT DOCUMENTS 8,394,101 B2 *    3/2013    Landes ........................ 606/84

* cited by examiner

*Primary Examiner* — Larry E Waggle, Jr.

(57) ABSTRACT

A discectomy instrument capable of removing portions of the spinal disc between adjacent vertebrae in a controlled manner that is efficient and easy to use. The discectomy instrument may include a handle, a rotary scraper, a barrel, a drive shaft, an outer sleeve and a retaining clip.

18 Claims, 2 Drawing Sheets

DISCECTOMY INSTRUMENT

CROSS-REFERENCE TO RELATED APPLICATIONS

The present application is a continuation of U.S. patent application No. 13/763,082 filed Feb. 8, 2013, which is a continuation of U.S. patent application No. 12/710,796, filed on Feb. 23, 2010, which issued as U.S. Pat. No. 8,394,101, which claims priority under 35 U.S.C. §119(e) to U.S. Provisional Patent Application Ser. No. 61/154,610, filed on Feb. 23, 2009. These applications are hereby incorporated by reference in their entireties for all purposes.

FIELD OF THE INVENTION

The present invention relates to an instrument for preparing the space between adjacent vertebrae to stabilize and support the spine.

BACKGROUND OF THE INVENTION

During spinal surgery, there is a need to remove portions of the spinal disc between adjacent vertebrae. Instruments are inserted into the disc space to remove portions of the disc by piercing the annulus and then the nucleus is mechanically disintegrated with the pieces being removed through suction, forceps, rongeurs, or other similar instruments.

There is a need for an instrument that allows for greater motion within the disc space to enable the nucleus to be disintegrated and removed with a minimal amount of time and ease of use for a surgeon.

SUMMARY OF THE INVENTION

In a preferred embodiment, the present invention provides a discectomy instrument that is capable of removing portions of the spinal disc between adjacent vertebrae in a controlled manner that is efficient and easy to use. The discectomy instrument preferably includes a handle, a rotary scraper, a barrel, a drive shaft, an outer sleeve and a retaining clip.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 1:
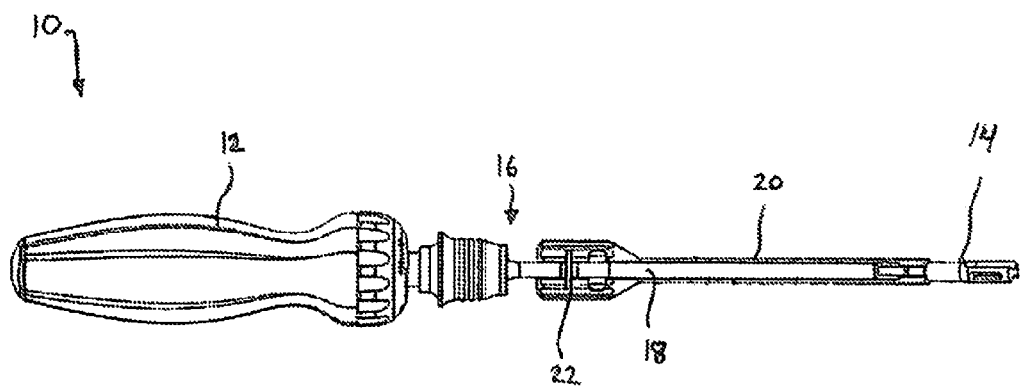
FIG. 1 is a bottom view of one embodiment of a discectomy instrument.
Figure 2:
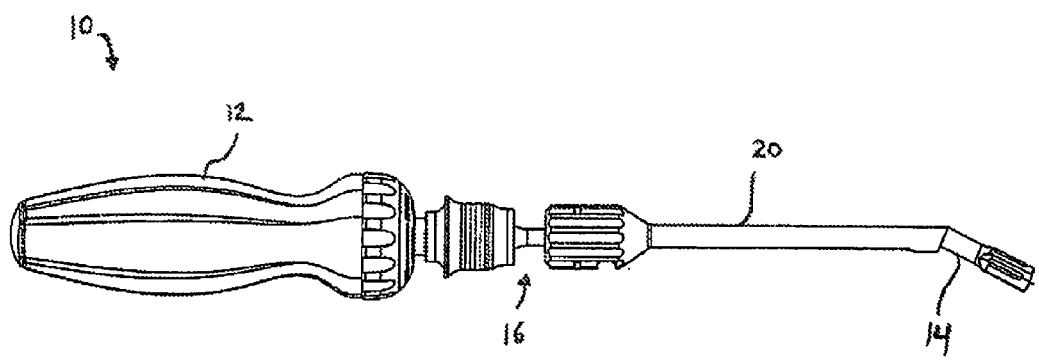
FIG. 2 is a side view of the discectomy instrument shown in FIG. 1.
Figure 3:
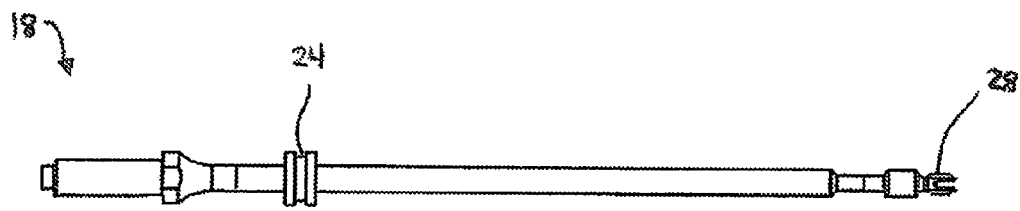
FIG. 3 is a side view of a drive shaft of the discectomy instrument shown in FIG. 1.
Figure 4:
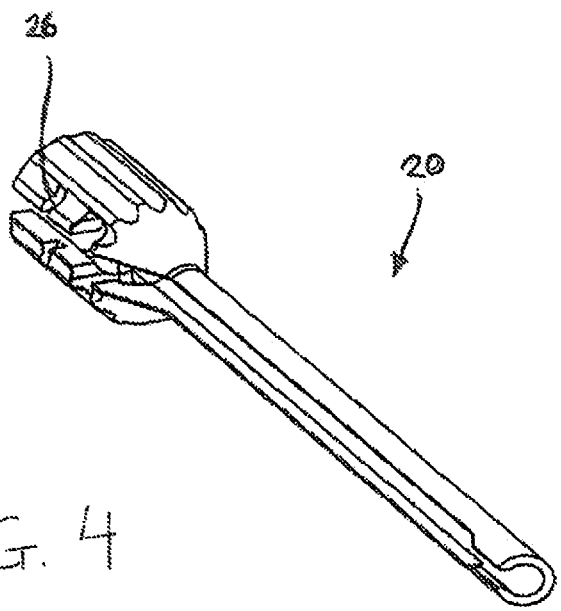
FIG. 4 is a perspective view of the outer sleeve of the discectomy instrument shown in FIG. 1.
Figure 5:
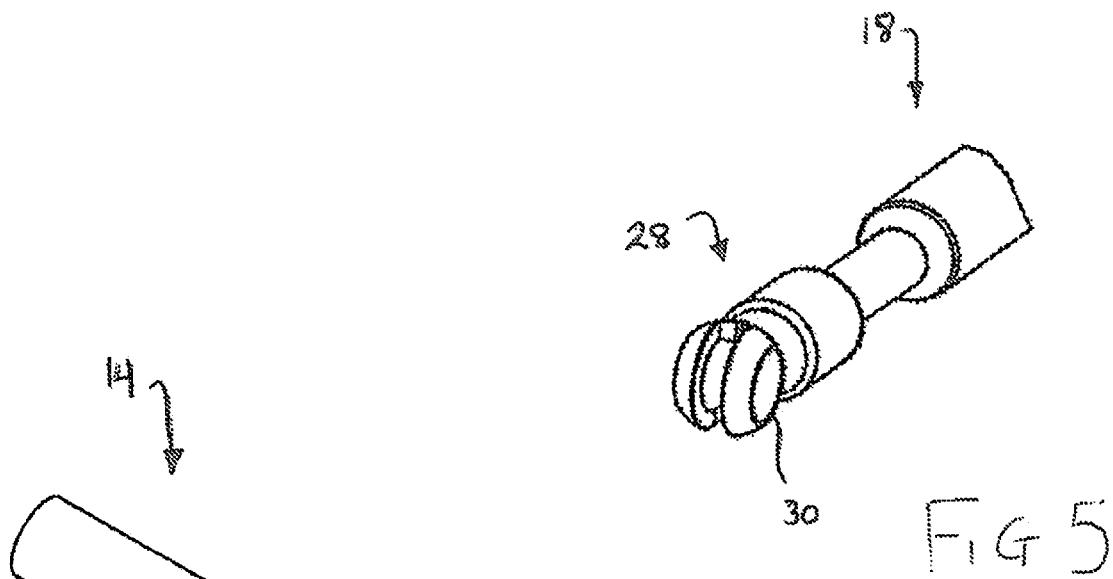
FIG. 5 is a close-up perspective view of the end of the drive shaft shown in FIG. 3.

With reference to FIGS. 1 and 2, a discectomy instrument 10 according to one embodiment of the present invention is illustrated. In a preferred embodiment, the discectomy instrument includes a handle 12, a rotary scraper 14, a barrel 16, a drive shaft 18, an outer sleeve 20 and a retaining clip 22. The handle 12 is preferably connected to a medial end of the drive shaft 18 through barrel 16 via an interference fit, snap fit, or similar connection that allows torque applied to handle 12 to transmit to drive shaft 18. Barrel 16 serves as a connection means and is moveable along a longitudinal axis defined by handle 12 and drive shaft 18. When moved along the axis in a direction towards the handle 12, the barrel will disengage the drive shaft 18 from the handle 12.

Located proximate to the barrel 16, is the outer sleeve 20 which receives the drive shaft 18. In a preferred embodiment, the outer sleeve 20 has a medial end and a distal end and is connected to the drive shaft 18 via a retainer clip 20 which connects to the drive shaft 18 and outer sleeve 20 in an interference fit. Turning to FIGS. 1-4, a retainer clip receiving portion 24 can be seen on the drive shaft 18 and a retainer clip receiving slot 26 can be seen on the outer sleeve 20. The outer sleeve is connected to the drive shaft 18 in a manner as to allow the drive shaft to rotate with respect to the outer sleeve 20 but not translate with respect to the outer sleeve 20. In a preferred embodiment, the distal end of the outer sleeve 20 includes an angled edge which is configured and dimensioned to support the rotary scraper 14 in a fixed position as discussed in further detail below.

Figure 6:
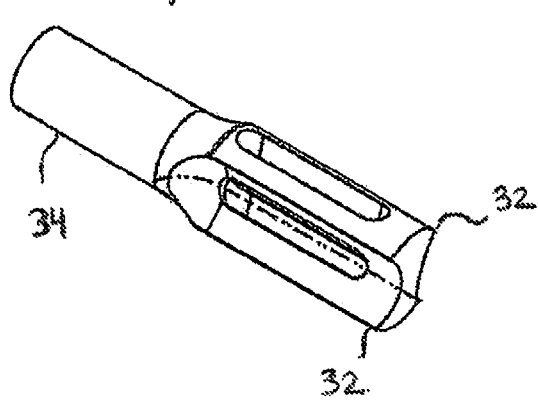
FIG. 6 is a close-up perspective view of the end of a rotary scraper of the discectomy instrument shown in FIG. 1.

With reference now to FIGS. 1-3 and 5, in a preferred embodiment, at a distal end of the drive shaft 18 is a ball joint 28. The ball joint 28 is coupled to the rotary scraper 14 at one end and to drive shaft 18 at the other end. The ball joint 28 includes a ball member 30, a first pin which forms the major ball axis and a second smaller pin which is oriented orthogonally to the first pin and extends through the ball member 30 as well as through the first pin. The pins along with the ball member 30 engage the rotary scraper 14. With additional reference to FIG. 6, the rotary scraper 14 includes at least one, but preferably a plurality of blades 32 on one end and a receiving portion 34 on the other end. The receiving portion 34 is configured and dimensioned to engage the first and/or second pins in the ball joint 28 and rest against the ball member 30. This engagement allows the rotary scraper 14 to pivot with respect to the drive shaft 18 as well as rotate with drive shaft 18.

As mentioned earlier, with the outer sleeve 20 in place surrounding the drive shaft 18, the distal end of the sleeve 20 engages the receiving end of the rotary scraper 14. The angled end of the outer sleeve 20 allows for the rotary scraper 14 to rotate but constrains the pivoting movement of the scraper 14 to a predetermined angle. This predetermined angle is a preferred cutting angle that is designed to maximize the cutting efficiency of the rotary cutter 14 during operation of the discectomy instrument 10.

In an exemplary use of the discectomy instrument 10, after the appropriate intervertebral disc has been identified and the appropriate surgical procedures have been undertaken to create a pathway to the intervertebral disc, the discectomy instrument 10 is introduced into the pathway until the rotary scraper 14 abuts the annulus of the intervertebral disc. The annulus of the disc is then pierced using the instrument 10 or another instrument capable of accomplishing the same task. The rotary scraper 14 of the discectomy instrument 10 is then inserted into the disc nucleus. Following insertion in to the disc nucleus, torque is applied to the handle 12 which in turn transmit the torque to the rotary scraper 14 via the drive shaft 18. As the rotary scraper 14 rotates, the blades 32 cut away portions of the disc nucleus, which may be removed using forceps, rongeurs, or a suction instrument. The process is continued until the desired portion of the disc nucleus is removed.

FIGS. 1-6 illustrate the features of the present device; however, these figures alone do not encompass other possible embodiments. For example, it is contemplated that in one embodiment, the outer sleeve 20 is configured to allow the rotary scraper 14 to articulate in a controlled manner rather than being limited to a fixed angle. In another embodiment, the outer sleeve 20 may be provided with an irrigation and suction channel (not shown) for removing portions of the nucleus while still allowing the rotary scraper 14 to articulate in a controlled manner. Additionally, the rotary scraper 14 can also include a channel (not shown) that is connected to the outer sleeve 20 which allows for the suction and irrigation of the disc space. Yet in another embodiment the rotary scraper 14 can be configured so as to be detachable allowing other tools to be attached to the distal end of the drive shaft 18.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A discectomy instrument for removing a portion of an intervertebral disc, comprising:
   a rotary scraper;
   a drive shaft operably attached to the rotary scraper;
   a ball joint coupled to the rotary scraper at one end and to the drive shaft at the other end, wherein the rotary scraper is pivotably connected to the ball joint; and
   a barrel, wherein the drive shaft is removably connected to the barrel and capable of transmitting torque, and wherein the rotary scraper is configured to pivot as well as rotate with the drive shaft.

2. The instrument of claim 1 further comprising an outer sleeve for coaxially receiving the drive shaft.

3. The instrument of claim 2, wherein the outer sleeve is connected to the drive shaft in a manner so as to allow the drive shaft to rotate with respect to the outer sleeve but not translate with respect to the outer sleeve.

4. The instrument of claim 2 further comprising a retaining clip that engages the drive shaft and the outer sleeve to connect the drive shaft to the outer sleeve in a rotatable, non-translatable manner.

5. The instrument of claim 2 further comprising a handle portion for being gripped by a user and operably attached to the rotary scraper.

6. The instrument of claim 5, wherein the handle and outer sleeve are coaxial and share a longitudinal axis.

7. The instrument of claim 6, wherein the barrel is configured to move along the longitudinal axis.

8. The instrument of claim 7, wherein when the barrel moves toward the handle, the barrel is configured to disengage the drive shaft from the handle, and when the barrel moves away from the handle, the barrel is configured to engage the drive shaft to the handle.

9. The instrument of claim 2, wherein the outer sleeve includes an angled edge configured and dimensioned to allow the rotary scraper to rotate but constrains pivoting movement at a predetermined angle.

10. The instrument of claim 1, wherein the rotary scraper comprises a plurality of blades.

11. A discectomy instrument for removing a portion of an intervertebral disc, comprising:
    a rotary scraper;
    a drive shaft operably attached to the rotary scraper;
    an outer sleeve for coaxially receiving the drive shaft; a ball joint coupled to the rotary scraper at one end and to the drive shaft at the other end, wherein the rotary scraper is pivotably connected to the ball joint; and
    a barrel, wherein the drive shaft is removably connected to the barrel and capable of transmitting torque, and wherein the rotary scraper is configured to pivot as well as rotate with the drive shaft.

12. The instrument of claim 11, wherein the outer sleeve is connected to the drive shaft in a manner so as to allow the drive shaft to rotate with respect to the outer sleeve but not translate with respect to the outer sleeve.

13. The instrument of claim 11 further comprising a retaining clip that engages the drive shaft and the outer sleeve to connect the drive shaft to the outer sleeve in a rotatable, non-translatable manner.

14. The instrument of claim 11 further comprising a handle portion for being gripped by a user and operably attached to the rotary scraper.

15. The instrument of claim 14, wherein the handle and outer sleeve are coaxial and share a longitudinal axis.

16. The instrument of claim 15, wherein the barrel is configured to move along the longitudinal axis such that when the barrel moves toward the handle, the barrel is configured to disengage the drive shaft from the handle, and when the barrel moves away from the handle, the barrel is configured to engage the drive shaft to the handle.

17. The instrument of claim 11, wherein the outer sleeve includes an angled edge configured and dimensioned to allow the rotary scraper to rotate but constrains pivoting movement at a predetermined angle.

18. The instrument of claim 11, wherein the rotary scraper comprises a plurality of blades.

* * * * *